United States Patent [19]
Naf

[11] 3,953,377
[45] Apr. 27, 1976

[54] ETHYL-2-TRANS-4-CIS UNDECADIENOATE, ETHYL-2-TRANS-4-CIS DODECADIENOATE AND ETHYL-2-DECADIENOATE PERFUME COMPOSITIONS

[75] Inventor: Ferdinand Naf, Geneva, Switzerland
[73] Assignee: Firmenich S.A., Geneva, Switzerland
[22] Filed: Aug. 27, 1974
[21] Appl. No.: 501,194

Related U.S. Application Data
[62] Division of Ser. No. 210,620, Dec. 21, 1971, Pat. No. 3,928,402.

[30] Foreign Application Priority Data
Dec. 22, 1970 Switzerland.................... 19018/70
Apr. 29, 1971 Switzerland.................... 6354/71

[52] U.S. Cl. ...................... 252/522; 260/410.9 R
[51] Int. Cl.² ........................................ C11B 9/00
[58] Field of Search ............... 252/522; 260/410.9 R

[56] References Cited
OTHER PUBLICATIONS
R. K. Creveling et al., J. Agr. Food Chem. 18, 19–24, 1970.
D. E. Heinz et al., J. Food Sci., 31, 69–71, 1966.

Primary Examiner—Veronica O'Keefe
Attorney, Agent, or Firm—Pennie & Edmonds

[57] ABSTRACT
Process for the preparation of $\gamma,\delta$-unsaturated carbonyl derivatives. Among the compounds prepared by the process of the present invention some are new and many possess interesting organoleptic properties.

4 Claims, No Drawings

ETHYL-2-TRANS-4-CIS UNDECADIENOATE, ETHYL-2-TRANS-4-CIS DODECADIENOATE AND ETHYL-2-DECADIENOATE PERFUME COMPOSITIONS

This is a division of application Ser. No. 210,620 filed Dec. 21, 1971 now U.S. Pat. No. 3,928,402.

SUMMARY OF THE INVENTION

The present invention relates to a new process for the preparation of γ,δ-unsaturated carbonyl compounds of formula

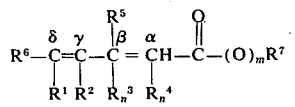

containing a single or a double bond in the α-position, said bond being represented by the dotted lines, and wherein a. the substituents $R^1$, $R^2$, $R^3$, $R^4$, $R^5$ and $R^6$ represent either a linear or branched, cyclic or acyclic, saturated or unsaturated univalent hydrocarbon radical, provided however that $R^3$ and $R^5$ do not possess a multiple bond in conjugation with the α,β-carbon-carbon bond, or a hydrogen atom, b. $R^7$ either has the meaning defined sub (a), c. the indexes $m$ and $n$ stand for zero of 1, and d. $R^3$, $R^4$ or $R^5$ may be linked to $R^7$ and form a cycloaliphatic ring.

The invention relates also to a process for the preparation of hydroxyl compounds of formula

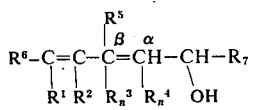

containing a single or a double bond in the α-position, and wherein the substituents $R^1$ to $R^7$, index $n$ and the dotted lines have the same meaning as given above.

The above mentioned processes of the present invention enable the preparation of a great variety of γ,δ-unsaturated carbonyl derivatives. Some of said derivatives are new and many possess interesting organoleptic properties. The invention also relates to the use of the above mentioned compounds as perfuming and fragrance-modifying agents for the manufacture of perfumes and perfumed products and as flavouring, taste-modifying and taste-enhancing agents for the manufacture of foodstuffs in general and artificial flavours for foodstuffs, animal feeds, beverages, pharmaceutical and tobacco products.

DESCRIPTION OF THE PREFERRED EMBODIMENTS

In accordance with the present invention, the process for the preparation of the compounds of formula I comprises treating an α,β-unsaturated carbonyl compound having the formula

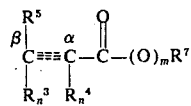

containing a double or a triple bond as represented by the dotted lines, and wherein the symbols $R^3$, $R^4$, $R^5$ and $R^7$, and the indexes $m$ and $n$ have the meaning defined for formula I, with an organometallic compound comprising a transition metal, a univalent cation and an alkenyl radical having the formula

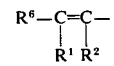

wherein $R^1$, $R^2$ and $R^6$ have the meaning defined above, to yield a carbonyl compound of formula I, wherein the geometrical configuration of the γ,δ olefinic double bond is identical to that of the double bond present in radical III of the starting organometallic compound.

In the above given formula II of the starting carbonyl derivatives, the univalent radicals represented by $R^3$, $R^4$, $R^5$ and $R^7$ include, for example, those derived from linear hydrocarbons such as, methyl, ethyl, n-propyl, isopropyl, n-butyl, isobutyl, n-pentyl, isopentyl, n-hexyl, isohexyl, n-heptyl, n-octyl, n-nonyl, n-decyl, n-undecyl and n-dodecyl. Equally, $R^3$, $R^4$, $R^5$ and $R^7$ can represent univalent radicals derived from linear or branched unsaturated hydrocarbons such as, for instance, buten-3-yl, penten-5-yl, hexen-6-yl, octen-7-yl, 3-ethyl-4-methylpenten-3-yl, 2,3-dimethylpenten-3-yl, 4-methyl-3-methylene-penten-4-yl, hexen-4-yl, 5-methylhexen-4-yl, 5-ethylhexen-3-yl, 4-ethylhexen-5-yl, 2,4-dimethyl-3-ethylpenten-3-yl, 2,4-dimethylpenten-3-yl, 2-methyl-3-methylene-penten-4-yl, 2,4-dimethyl-3-methylene-penten-4-yl, 3,4-dimethylhexen-3-yl, 5-ethylhexen-4-yl, 3,5-dimethylhexen-3-yl, 3,6-dimethylhexen-3-yl, 2,3-dimethylhexen-4-yl and 2,5-dimethylhexen-4-yl.

In formula II, $R^3$, $R^4$ or $R^5$ may be linked to $R^7$ and form, for instance, together with their carrier carbon atoms, lactones or cycloaliphatic rings. In formula III representing the alkenyl radical of the starting organometallic compound, $R^1$, $R^2$ and $R^6$ may include, for example, the same hydrocarbon radicals as those mentioned above for the substituents $R^3$ to $R^5$ and $R^7$. A preferred group of hydrocarbon radicals includes methyl propyl, pentyl or heptyl.

New synthetic methods, recently appeared in the chemical literature, have enabled the selective formation of carbon - carbon bonds between unlike organic groups [see, for example, J.Am.Chem.Soc., 89, 3911 (1967); idem, 90, 5615 (1967); idem, 39, 4245 (1967); idem, 90, 5618 (1968); Tetrahedron Letters, 315 (1970)]. Said methods involve the reaction of anionic organometallic reagents containing copper, and they have been generally applied to obtain saturated or unsaturated hydrocarbons by reacting an alkyl or alkenyl halide with a copper organometallic reagent comprising alkyl groups [J.Am.Chem.Soc., 91, 4871 (1969)]. We have now surprisingly found that by treating an α,β-unsaturated carbonyl derivative of formula II with an organometallic compound comprising a transition metal, a univalent cation and an alkenyl radical of formula III, a γ,δ-unsaturated carbonyl compound of formula I was obtained; in said compound the geometrical configuration of the γ,δ olefinic double bond is identical to that of the double bond present in radical III. The process according to the present invention enables therefore the specific formation of γ,δ olefinic carbonyl derivatives in their pure cis- or trans- isomeric form.

The theoretical reasons as well as the mechanism of the aforementioned reaction, which characterizes the new process of the present invention, are so far badly understood and do not find an analogy with previously known chemical reactions, However, it seems likely that the critical property of the organometallic reagent, able to promote the chemical process in accordance with the present invention, is the availability of one or two non-bonding electrons from the d-orbitals of the metal comprised in said organometallic reagent.

In fact, suitable organometallic compounds include transition metal derivatives such as, e.g., copper (I), manganese (II), iron (II) or nickel (II) in combination with an alkenyl group and a univalent cation.

Said organometallic derivatives may be represented by the following stoichiometric formula

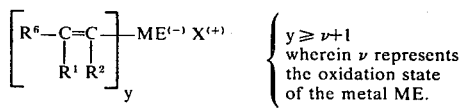

$y \geq \nu+1$
wherein $\nu$ represents the oxidation state of the metal ME.

wherein the symbol ME represents a metal of the recited type, $X^{(+)}$ represents a univalent cation such as, e.g., $Li^{(+)}$, $[Mg\text{-halogen}]^{(+)}$ or a substituted or unsubstituted ammonium group, and the substituents $R^1$, $R^2$ and $R^6$ have the same meaning as that previously indicated for formula III. However, it must clearly be understood that the real chemical structure of the above mentioned organometallic derivatives is not known with accuracy.

$Li^{(+)}$ and $[Mg\text{-halogen}]^{(+)}$ represent the preferred cation and copper (I) is used preferentially as transition metal.

The reaction of the starting carbonyl compound of formula II with the organometallic reagent is better carried out in a suspension or a solution in an organic solvent.

We have found that the solubility or, simply, the reactivity of the organometallic derivatives, used in accordance with the process of the present invention, may be enhanced by using certain specific complexing agents, such as, e.g., phosphines or alkyl phosphites.

For both practical and economical reasons, a preferred class of said complexing agents includes tri-n-butyl phosphine and trimethyl phosphite. This latter reagent possesses the advantage of being a liquid of low boiling point, easily enabling therefore its recovery on distilling it once the reaction is over.

Many organic solvents may conveniently act as complexing agents in much the same extent as the aforementioned agents. For example, it is possible to use ethers, such as diethyl ether, tetrahydrofurane or dioxane, acetals such as dimethoxyethane or a mixture of at least two of said solvents. The reaction is preferably carried out in diethyl ether.

The temperature at which the above mentioned reaction can be carried out may vary within wide limits and is comprised in between about 0° and about −100° C, however, said temperature range is not deemed to be restrictive and temperatures higher or lower than the above given range may be used. It must be noted that at temperatures higher than 0° C the organometallic reagents may decompose and at temperatures lower than −100° C the reaction time increases considerably. Specifically, the above reaction may be carried out at preferential temperatures comprised in between about −5° and about −35° C. Moreover, in the course of the reaction the reacting mixture is preferably kept under an atmosphere of an inert gas such as nitrogen or argon.

A class of compounds of formula II, used as starting materials in the presently disclosed process, includes unsaturated aldehydes and ketones as well as esters, lactones and acyl halides comprising at least a multiple bond in the $\alpha,\beta$-position, relative to the carbonyl group.

A preferred class of compounds of formula II includes acetylenic esters, such as ethyl or methyl propiolate, ethylenic esters, such as ethyl or methyl acrylate, aldehydes, such as acrolein, and ketones, such as 3-methyl-cyclohexen-2-one, methyl vinyl ketone, $\beta,\beta$-dimethylvinyl ketone or methyl 2-methylene-3-oxo-cyclopentylacetate. Most of the compounds of formula II are cheap commercially available products. Whenever required, their synthesis can be carried out according to known methods [see, for example, "Organic Reactions", John Wiley & Sons, Inc., New York].

Equally, the alkenyl halides used as starting materials for the preparation of the organometallic compounds, employed for carrying out the process of the present invention, may be obtained according to well known synthetic methods [see, e.g. J.Am.Chem.Soc., 55, 4279 (1933); J.Chem.Soc. 2082 (1951), and J.Am.Chem.Soc., 75, 632 (1953)].

The starting organometallic reagents may be prepared by the reaction of an alkenyl halide with lithium metal followed by the treatment of the obtained lithium derivative with copper (I) iodide. The method followed is analogous to that described in J.Org.Chem. 17, 1630 (1952) and Rec. Trav. chim. Pays-Bas, 55, 821 (1936) and is better illustrated by the examples given hereinafter.

As said above, the process of the present invention has the great advantage of being stereospecific. By proceeding through specific stereo isomers, said process eliminates the expensive purification which was necessary whenever ordinary synthetic routes were applied, and offers therefore a very convenient and economical industrial method.

Another interest of the process of the present invention is that it enables the preparation of a great variety of compounds possessing a high interest particularly for the perfumery and/or the flavour industry. Said compounds may be directly used as such as perfuming and/or as flavouring agents or as ingredients for the preparation of perfuming or flavouring mixtures or compositions. The compounds of formula I may also represent useful intermediates for the preparation of other compounds which possess interesting organoleptic properties. Such is the case, for instance, for the compounds of formula I wherein $R^7$ is hydrogen and the index $m$ stands for 1 (= acid derivatives) which can be easily converted into their ester derivatives. Equally, certain ketones or aldehydes represented by formula I may, according to commonly known synthetic methods, be converted into their corresponding alcohols [see, e.g. Cram and Hammond, Organic Chemistry, McGraw Hill Inc., New York (1959), pp. 74, 280].

In accordance with the present invention, the process for the preparation of the hydroxyl derivatives of formula IV, comprises reducing a carbonyl compound having the formula I wherein m is zero. Said reduction can be carried out by means of the reagents commonly used in organic chemistry for selectively reducing the carbonyl fonction in the presence of an olefinic double bond. A class of said reducing agents includes certain metal hydrides such as, e.g., lithium aluminium hydride, sodium or lithium hydride.

Further, the esters of formula I may be subjected to hydrolysis or transesterification to afford the corresponding acids or other esters respectively. The following table illustrates some of the compounds which can be obtained by the process of the present invention. The starting materials as well as the organoleptic characters and/or the physical constants of the products are indicated.

| $\gamma,\delta$-Unsaturated carbonyl products I[1] | Starting materials Alkenyl radical III of the organometallic derivative[2] |
|---|---|
| a. ALDEHYDES | |
| Penten-4-al | $CH_2=CH-$ |
| Pentadien-2,4-al trans, trans | " |
| Hepten-4-al cis | $CH_3-CH_2-CH=CH-$ |
| Heptadien-2,4-al trans, trans | $CH_3-CH_2-CH=CH-$ |
| Octen-4-al cis | $CH_3-(CH_2)_2-CH=CH-$ |
| Nonen-4-al cis | $CH_3-(CH_2)_3-CH=CH-$ |
| Nonadien-2,4-al trans, trans | " |
| Decen-4-al cis | $CH_3(CH_2)_4-CH=CH-$ |
| 3-Methyl-decen-4-al trans | " |
| Undecen-4-al cis | $CH_3-(CH_2)_5-CH=CH-$ |
| Dodecen-4-al cis | $CH_3-(CH_2)_6-CH=CH-$ |
| Pentadecen-4-al cis | $CH_3-(CH_2)_9-CH=CH-$ |
| b. KETONES | |
| Octen-5-one-2 cis | $CH_3-CH_2-CH=CH-$ |
| Octadien-3,5-one-2 trans, trans | " |
| Octadien-5,7-one-2 cis, cis | $CH_2=CH-CH=CH-$ |
| Undecen-5-one-2 cis | $CH_3-(CH_2)_4-CH=CH-$ |
| Undecadien-5,8-one-2 cis, cis | $CH_3-CH_2-CH=CH-CH_2-CH=CH-$ |
| c. ACIDS AND ESTERS | |
| Ethyl sorbate | $CH_3-CH=CH-$ |
| Methyl hexen-4-oate cis | " |
| Ethyl hexen-4-oate cis | " |
| Methyl hexadien-2,4-oate trans, cis | " |
| Ethyl hexadien-2,4-oate trans, cis | " |
| Methyl hepten-4-oate cis | $CH_3-CH_2-CH=CH-$ |
| Ethyl hepten-4-oate cis | " |
| Methyl heptadien-2,4-oate trans, cis | " |
| Ethyl heptadien-2,4-oate trans, cis | " |
| Methyl octen-4-oate cis | $CH_3-(CH_2)_2-CH=CH-$ |
| Ethyl octen-4-oate cis | " |
| Methyl octadien-2,4-oate trans, cis | " |
| Ethyl octadien-2,4-oate trans, cis | " |
| Octadien-2,4-oic acid trans, trans | $CH_3-(CH_2)_2-CH=CH-$ |
| Octen-4-oic acid trans | " |
| Octen-4-oic acid cis | " |
| Methyl nonen-4-oate cis | $CH_3-(CH_2)_3-CH=CH-$ |
| Ethyl nonen-4-oate cis | " |
| Methyl nonadien-2,4-oate trans, cis | " |
| Ethyl nonadien-2,4-oate trans, cis | " |
| Methyl decen-4-oate cis | $CH_3-(CH_2)_4-CH=CH-$ |
| Ethyl decen-4-oate cis | " |
| Methyl decadien-2,4-oate trans, cis | " |
| Ethyl decadien-2,4-oate trans, cis | " |
| Ethyl decadien-2,4-oate trans, trans | " |
| Propyl decadien-2,4-oate trans-2, cis-4 | " |
| Isopropyl decadien-2,4-oate trans-2, cis-4 | " |
| Butyl decadien-2,4-oate trans-2, cis-4 | " |
| Amyl decadien-2,4-oate trans-2, cis-4 | " |
| 3-Methyl-decen-4-oic acid trans | " |
| 3-Methyl-decen-4-oic acid cis | " |
| Methyl undecen-4-oate cis | $CH_3-(CH_2)_5-CH=CH-$ |
| Ethyl undecen-4-oate cis | " |
| Methyl undecadien-2,4-oate trans, cis | " |
| Ethyl undecadien-2,4-oate trans, cis | " |
| Methyl dodecen-4-oate cis | $CH_3-(CH_2)_6-CH=CH-$ |
| Methyl dodecadien-2,4-oate trans, cis | " |
| Ethyl dodecadien-2,4-oate trans, cis | " |
| 3-Methyl-3-propen-1-yl-cyclohexanone cis | $CH_3-CH=CH-$ |
| 3-Methyl-3-buten-1-yl-cyclohexanone cis | $CH_3-CH_2-CH=CH-$ |
| 3-Methyl-3-penten-1-yl-cylcohexanone cis | $CH_3-(CH_2)_2-CH=CH-$ |
| 3-Methyl-3-hexen-1-yl-cyclohexanone cis | $CH_3-(CH_2)_3-CH=CH-$ |
| d. ALCOHOLS | |
| Hexadien-2,4-ol trans, trans | |
| 3-Methyl-decen-4-ol trans | |
| 3-Methyl-decen-4-ol cis | |

| Starting materials $\alpha,\beta$-Unsaturated carbonyl derivative II | Physical constants[3] | Organoleptic character |
|---|---|---|
| $CH_2=CH-CHO$ | 103-4/740 | green, vegetable note |
| $CH\equiv C-CHO$ | 36-7/20, $n_D^{20}=1,4516$ | green |
| $CH_2=CH-CHO$ | 42/10, $n_D^{20}=1,4405$ | green, fatty, fruity, vegetable note |
| $CH\equiv C-CHO$ | 58-60/5 | |
| $CH_2=CH-CHO$ | | |
| " | 72/10 | green, fatty |
| $CH\equiv C-CHO$ | 72-4/3 | green, fatty, oily |
| $CH_2=CH-CHO$ | 89/11, $n_D^{20}=1,4441$ | calamus, fatty |
| $CH_3-CH=CH-CHO$ | $d_4^{20}=0,8361$; $n_D^{20}=1,4418$ | aldehyde like |
| $CH_2=CH-CHO$ | 94/10 | calamus, pansy, fatty |
| " | 60/0,001, $n_D^{20}=1,4545$ | green, woody, fatty |

| Starting materials α,β-Unsaturated carbonyl derivative II | Physical constants[3] | Organoleptic character |
|---|---|---|
| " | 85/0,001 | green, weak |
| $CH_2=CH-CO-CH_3$ | 56-8/12 | fatty, green, lactone like |
| $CH\equiv C-CO-CH_3$ | SM: $M^+ = 124$ | fatty, coconut |
| $CH_2=CH-CO-CH_3$ | 62-7/5 | |
| " | 38/0,001 | fatty, spicy, anise like |
| " | 32/0,001, $n_D^{20} = 1,4618$ | green, fatty, cheese |
| $CH\equiv C-COOC_2H_5$ | 87-8/18 | fruity, spicy |
| $CH_2=CH-COOCH_3$ | 40/11 | |
| $CH_2=CH-COOC_2H_5$ | 54-5/11 | |
| $CH\equiv C-COOCH_3$ | 57/11 | |
| $CH\equiv C-COOC_2H_5$ | 68-70/11 | myrrh, fruity, strawberry |
| $CH_2=CH-COOCH_3$ | 55/11 | |
| $CH_2=CH-COOC_2H_5$ | 67-8/11 | |
| $CH\equiv C-COOCH_3$ | 73/11 | |
| $CH\equiv C-COOC_2H_5$ | 83-7/11 | |
| $CH_2=HC-COOCH_3$ | 72/11 | fruity, fatty |
| $CH_2=CH-COOC_2H_5$ | 78-9/11 | fruity, fatty, green, pineapple, pear |
| $CH\equiv C-COOCH_3$ | 88/11 | green, fruity |
| $CH\equiv C-COOC_2H_5$ | 37/0,001 | green, fruity |
| $CH\equiv C-COOH$ | F. 76° | |
| $CH_2=CH-COOH$ | 93/1,5 | |
| " | 96/0,8 | |
| $CH_2=CH-COOCH_3$ | 85/11 | |
| $CH_2=CH-COOC_2H_5$ | 100/11 | |
| $CH\equiv C-COOCH_3$ | 46/0,05 | |
| $CH\equiv C-COOC_2H_5$ | 56/0,05 | |
| $CH_2=CH-COOCH_3$ | 100/11 | |
| $CH_2=CH-COOC_2H_5$ | 130/12 | fruity, pineapple, pear, fatty, green |
| $CH\equiv C-COOCH_3$ | 46/0,001 | fruity, fatty |
| $CH\equiv C-COOC_2H_5$ | 70-2/0,05 | fruity, pear |
| " | 79/0,08 | fruity, fatty |
| $CH\equiv C-COOC_3H_7^n$ | 54-6/0,001 | fruity, pear |
| $CH\equiv C-COOC_3H_7^i$ | 65/0,002 | pear |
| $CH\equiv C-COOC_4H_9$ | 69/0,001 | fatty, fruity |
| $CH\equiv C-COOC_5H_{11}$ | 118/0,06 | fatty, fruity |
| $CH_2=CH-COOH$ | $d_4^{20} = 0,8951; n_D^{20} = 1,4473$ | fatty, candle |
| " | $d_4^{20} = 0,8958; n_D^{20} = 1,4470$ | |
| $CH_2=CH-COOCH_3$ | 115/11 | |
| $CH_2=CH-COOC_2H_5$ | 129/11 | |
| $CH\equiv C-COOCH_3$ | 95/0,05 | floral, amber like, fruity |
| $CH\equiv C-COOC_2H_5$ | 89/0,05 | floral, amber like, fruity |
| $CH_2=CH-COOCH_3$ | 130/11 | |
| $CH\equiv C-COOCH_3$ | 95/0,05 | |
| $CH\equiv C-COOC_2H_5$ | 100-2/0,05 | fatty, weakly fruity, violet, green |
| 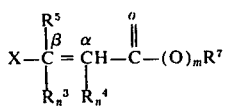 | 73/11 | |
| " | | |
| " | 60/0,005 | |
| " | | |
| | 82-3/18 | apple |
| | 112-3/10 | floral, fatty, rose, wax |
| | $d_4^{20} = 0,8359; n_D^{20} = 1,4496$ | |

[1]The geometrical configuration of the ethylenic double bonds is given in the order: 2-position, 4-position.
[2]The geometrical configuration of the ethylenic double bond of alkenyl radical III is identical to that indicated for the ethylenic double bond in the 4-position of carbonyl compound I.
[3]Except where otherwise stated, the given boiling points are indicated in degrees centigrade. Pressure is indicated in Torr units; °C/Torr.

In accordance with a variation of the process of the present invention, the compounds of formula I are obtained by treating a carbonyl compound having the formula $$X-\underset{R_n^3}{\underset{|}{C}}=\underset{R_n^4}{\underset{|}{CH}}-\overset{O}{\overset{\|}{C}}-(O)_m R^7 \qquad V$$

containing a single or a double bond in the α-position, and wherein the substituents $R^3$ to $R^5$ and $R^7$, and indexes $m$ and $n$ have the same meaning as given for formula II, and the symbol X represents a halogen atom, with an organometallic compound comprising a transition metal, a univalent cation and an alkenyl radical of formula III.

It must be noted that in this case also the geometrical configuration of the γ, δ olefinic double bond of obtained compounds I is identical to that of the double bond present in radical III.

Suitable organometallic compounds include the same reagents as those mentioned hereinabove. The embodiment of the presently disclosed process is analogous to that previously described for the reaction of carbonyl compounds Ii with the same organometallic reagents.

Compounds of formula V may be prepared according to known synthetic methods [see, for example, Ann., 179, 85 (1875); Ann., 193, 31 (1878); Ber., 15, 2702 (1882); Bull. Soc. Chim. France, 594 (1948)].

The invention also relates to the use of the compounds of formula I which are new as perfuming, and/or flavouring agents. Said new compounds of formula I include — methyl and ethyl 4-cis-hexenoate, methyl and ethyl 2-trans-4-cis-hexadienoate, methyl and ethyl 4-cis-heptenoate, methyl and ethyl 2-trans-4-cis-heptadienoate, methyl and ethyl 2-trans-4-cis-octadienoate, methyl and ethyl 4-cis-noneoate, methyl and ethyl 2-trans-4-cis-nonadienoate, methyl and ethyl 4-cis-undecenoate, methyl and ethyl 2-trans-4-cis-undecadienoate, methyl and ethyl 2-cis-4-cis-undecadienoate, methyl and ethyl 4-cis-dodecenoate, methyl and ethyl 2-trans-4-cis-dodecadienoate, ethyl 2-trans-4-trans-dodecadienoate, methyl and ethyl 2-trans-4-cis-tridecadienoate, methyl and ethyl 4-cis-tridecenoate, methyl and ethyl 2-trans-4-cis-tetradecadienoate, methyl and ethyl 4-cis-tetradecenoate, methyl and ethyl 2-trans-4-cis-pentadecadienoate, methyl and ethyl 4-cis-pentadecenoate, methyl and ethyl 2-trans-4-cis-hexadecadienoate, methyl and ethyl 4-cis-hexadecenoate, 3-methyl-3-[cis-propen-1-yl]-1-cyclohexanone, 3-methyl-3-[cis-buten-1-yl]-1-cyclohexanone, 3-methyl-3-[cis-penten-1-yl]-1-cyclohexanone and 3-methyl-3-[cis-hexen-1-yl]-1-cyclohexanone, cis-5-nonen-2-one, 4,4-dimethyl-5-cis-hepten-2-one.

More particularly, the process in accordance with the present invention enables the preparation of alkyl 2-[penten-2-yl]-3-oxo-cyclopentylacetates. Said compounds, particularly methyl 2-[cis-penten-2-yl]-3-oxo-cyclopentylacetate, known in the art of perfumery as methyl jasmonate, possess valuable odoriferous properties. The preparation of said cyclopentylacetate derivatives is illustrated by the following reaction scheme:

derivatives. More specifically, by the hereinabove method, it is possible to obtain methyl 2-pentyl-3-oxo-cyclopentylacetate in its cis- or trans- cyclanic isomeric form. Said compound is better known in the art of perfumery under the name of methyl dihydrojasmonate.

The cyclic ketone, used as starting material in the above described process, may be synthesized, for instance, in accordance with the method described in Bull. Chem. Soc. Japan, 30, 450–4 (1957).

Among the compounds of formula I which are not new but for which we have found a novel, interesting and unexpected use, we have to mention, for example, the methyl and ethyl esters of the decadienoic and octenoic acid (see given Table).

The compounds mentioned above possess very interesting organoleptic properties and, as a consequence, they may be used as flavouring and taste-modifying agents, in the manufacture of artificial flavours for foodstuffs, beverages, animal feeds, pharmaceuticals and tobacco. The term "foodstuff" is used broadly; for example, the compounds of the invention may be incorporated into products such as coffee, tea and cocoa.

Depending upon the nature of the products to which they are added, they can develop or enhance flavour notes, such as green and fruity notes; moreover, they can impart to said products a fruity character reminiscent of pears.

The proportions of said compounds to be used in such compositions can vary within wide limits, and are

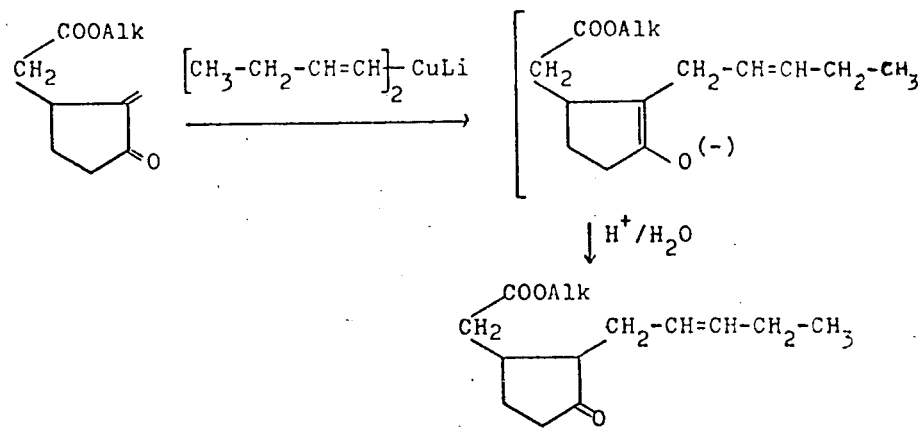

Depending upon the specific conditions used for carrying out the acidification of the enolate intermediate, the obtained compounds possess the cis- or trans-cyclanic isomeric configuration. Said isomers may be represented by the following formulae:

dependent on the desired specific result. For example, interesting flavouring effects can be achieved with amounts ranging from 1 to 10 ppm, based on the total weight of the product flavoured. However, special effects may be achieved by proportions as high as 100 or

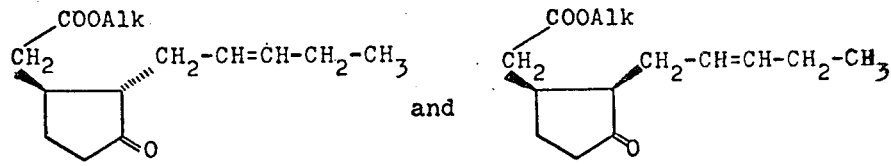

Upon reduction of the olefinic double bond of the obtained cyclopentylacetate derivatives according to commonly known hydrogenation techniques [see, e.g., H.O. House, Modern Synthetic Reactions, Benjamin, Inc., New York (1965), p. 1 and foll.], said derivatives may be converted into their corresponding 2-pentyl even 1000 ppm. For the manufacture of synthetic flavouring compositions, the proportions can be as high as 5% of the total weight of the composition.

The mentioned compounds may be used as odoriferous ingredients in concentrated or diluted perfumes and in perfumed products such as soaps, detergents, cosmetics and waxes; in fact, in a wide range of manufactured products which they can render commercially more attractive.

The proportions of the new compounds to be used for perfuming purposes can also vary widely. Typically, interesting perfuming effects can be obtained by proportions ranging from about 1000 ppm to about 5% or even more, based on the total weight of the perfumed product.

In all cases, the ranges given above may be varied, depending upon the specific odoriferous or flavouring effect it is desired to achieve.

The invention is better illustrated by the following examples, in which all the given temperatures are indicated in degrees centigrade. In said examples the term "vapour phase chromatography" is abbreviated to read VPC.

EXAMPLE 1

Ethyl 2-trans-4-cis-decadienate

Cis-hepten-1-yl bromide (11.15 g.; 63 mMole), containing 98% of the cis isomer, in anhydrous ether (30 ml.) was added dropwise at −10°, in an argon atmosphere under vigourous stirring, to a suspension of lithium metal (0.88 g.; 176 matomg.), containing 1.5% of sodium metal, in anhydrous ether (30 ml.). The resulting solution was added dropwise at −10° to a suspension of copper$^{(I)}$-iodide powder (6.4 g.; 32 mMole in anhydrous ether (80 ml.). To this reaction mixture, kept at −10° under argon, a solution of ethyl propiolate (3.14 g.; 32 mMole) in anhydrous ether (20 ml.) was then added over a period of 5 minutes.

At reaction completion the reaction mixture was stirred 10 minutes more. Then it was poured onto a mixture of a 2N aqueous hydrochloric acid solution and ice and the obtained precipitate was separated by filtration. The aqueous layer was extracted with ether and the combined organic extracts were evaporated after being washed and dried according to usual techniques. The residue was distilled and afford a colourless oil (5.7 g.; 90% yield), B.p. 70°–72°/0.05 Torr. A VPC analysis of the above distilled product showed a content of 95% of ethyl 2-trans-4-cis-decadienate.

IR: 3020, 1715, 1710, 1635, 1600, 990 cm$^{-1}$

NMR: 0.92 (3H), 1.27 (3H, t, J = 6.5 cps), 2.0-2.5 (2H, m), 4.15 (2H, q, J = 7 cps), 5.8 (1H, d, J = 15 cps), 5.5-6.3 (2H, m), 7.55 (1H, d/d, J = 15 cps, J' = 11 cps) δ ppm.

MS: M$^+$ = 196 (36), m/e = 167 (2.8), 157 (40), 139 (2.8), 125 (77), 108 (22), 97 (71), 81 (100), 67 (83), 55 (44), 41 (60), 29 (97).

UV: $\gamma_{max}^{EtOH}$ = 265.0 mμ; ε = 24,800

Cis-hepten-1-yl bromide, used as strating material for the above preparation, can be synthetized as follows:

Bromine (308 g.; 1.9 Mole) was added dropwise, under vigourous stirring, to a solution of 2-octenoic acid (260 g.; 1.83 Mole) in carbon disulfide (270 ml.) at a temperature comprised in between 0° and +5°. After being kept overnight at room temperature, the reaction mixture was concentrated under reduced pressure. The obtained residue (508 g.) was dissolved in an aqueous alkaline solution (265 g. of NaOH in 1250 ml. of water) and then steam distilled. An important gas evolution was observed during the last operation.

The resulting aqueous layer was extracted with pentane and the organic extracts were then combined with the organic layer of the obtained distillate. 95% pure cis-hepten-1-yl bromide (108 g.; 41% yield) was obtained by evaporation of the volatile components and subsequent distillation of the obtained residue. B.p. 45°–47°/11 Torr. $n_D^{20}$ = 1.4594; $d_{20}^{20}$ = 1.553

EXAMPLE 2

Ethyl 2-trans-4-cis-dodecadienoate i. lithium metal (0.88 g.; 126 matomg.) containing 1.5% of sodium metal
ii. cis-nonen-1-yl bromide (12.9 g.; 63 mMole) containing 89% of the cis isomer
iii. copper$^{(I)}$-iodide (6.4 g.; 32 mMole) and
iv. ethyl propiolate (13.4 g.; 32 mMole) were treated according to the procedure as given in Example 1. The resulting reaction mixture contained 84% of ethyl 2-trans-4-cis-dodecadienoate and 16% of the 2-trans-4-trans isomer. The distillation of the crude mixture gave a colourless oil (5.76 g.; 80% yield, B.p. 100°–102°/0.05 Torr, containing 80% of ethyl 2-trans-4-cis-dodecadienoate.

IR (liquid): 3010, 1713, 1635, 1600 and 990 cm$^{-1}$

NMR: 0.88 (3H), 1.26 (3H, t, J = 7 cps), 1.8-2.4 (2H), 4.10 (2H, q, J = 7 cps), 5.75 (1H, d, J = 15 cps), 5.5-6.3 (2H, m), 7.49 (1H, d/d, J = 15 cps, J' = 11 cps) δ ppm MS: M$^+$ = 224 (32); m/e = 195 (1), 179 (37), 167 (4), 150 (12), 136 (26), 125 (100) 97 (74), 81 (96), 67 (90), 55 (60), 41 (69), 29 (89).

Cis-nonen-1-yl bromide, used as starting material for the above preparation, was obtained as described in Example 1 for cis-hepten-1-yl bromide, nonen-2-oic acid being used as starting material.

EXAMPLE 3

Ethyl 4-cis-decenoate

Cis-hepten-1-yl bromide (5.6 g.; 32 mMole), containing 98% of the cis isomer, in anhydrous ether (8 ml.) was added dropwise at −10°, in an argon atmosphere under vigourous stirring to a suspension of lithium metal (0.44 g.; 63 matomg.), which contained 1.5% of sodium metal, in anhydrous ether (8 ml.). The resulting solution was then added dropwise at −25° − −30° to a suspension of trimethylphosphite iodocuprate (stoichiometric formula = [(CH$_3$O)$_3$P]$_2$CuI) (7.3 g.; 16 mMole) in anhydrous ether (50 ml.). The addition was carried out at such a speed as to constantly keep the colour of the solution dark red. To this reaction mixture, kept at −40°, was then added over a period of 30 minutes a solution of ethyl acrylate (1.6 g.; 16 mMole) in anhydrous ether (10 ml.). The reaction was slightly exothermic.

After 40 more minutes stirring, the reaction mixture was poured onto an excess of a saturated aqueous ammonium chloride solution. The aqueous layer was treated as described in Example 1 and the residue obtained by evaporation was filtered on a silicagel column (50 g.). After elution with a 4 : 1 mixture of hexane and diethylether and subsequent evaporation, the resulting colourless oil was eluted again on a silicagel column (50 g.) with a 95 : 5 hexane-ether mixture, to afford after the usual treatments ethyl 4-cis-decenoate (1.2 g.; 38% yield), B.p. 130°/12 Torr. The collected product was isomerically pure.

IR (liquid): 3005, 1753, 725 cm$^{-1}$

NMR: 0.88 (3H), 1.22 (3H, t, J = 7 cps), 1.8-2.4 (6H) 4.02 (2H, 2, J = 7 cps), 5.28 (2H, m) δ ppm MS: M$^+$ = 198 (9); m/e = 169 (< 1), 125 (46), 135 (20) 123 (15), 110 (93), 96 (51), 88 (100), 84 (53), 69 (91), 55 (93), 41 (90), 29 (95).

Cis-hepten-1-yl bromide, used as starting material for the above preparation, was synthetized as shown in Example 1.

EXAMPLE 4

Ethyl 4-cis-octenoate i. lithium metal (0.88 g.; 126 matomg.) containing 1.5% of sodium metal
ii. cis-penten-1-yl bromide (9.5 g.; 63 mMole)
iii. trimethylphosphite iodocuprate (14.6 g.; 32 mMole) and
iv. ethyl acrylate (3.2 g.; 32 mMole)
were treated in the same way as described in Example 3. Distillation of the reaction mixture gave ethyl 4-cis-octenoate (1.47 g.; 27% yield), B.p.78°–9°/11 Torr and diethyl α-(cis-hexen-2-yl)-glutarate (2.7 g.; 31% yield. B.p. 105°–120°/0.01 torr.).

Ethyl 4-cis-octenoate:
IR: 3010, 1735 $cm^{-1}$
NMR: 0.9 (3H, t, J = 6cps), 1.22 (3H, t, J = 7 cps), 1.85-2.4 (6H), 4.03 (2H, q, J = 7 cps), 5.2-5.4 (2H) δ ppm
MS: $M^+$= 170 (8.7); m/e = 141 (3), 124 (41), 113 (3.4), 96 (46), 88 (66), 82 (69), 67 (45), 55 (100), 41 (64), 29 (69)

α-(cis-hexen-2-yl)-glutarate:
IR: 3010, 1730 $cm^{-1}$
NMR: 0.89 (3H, t, J = 6 cps), 1.20 (6H, t, J = 7 cps), 1.7-2.5 (7H), 4.06 (4H, q, J = 6 cps), 5.2-5.5 (2H) δ ppm
MS: $M^+$ = 270 (0); m/e = 225 (3.7), 196 (5.6), 151 (3.2), 139 (3.7), 122 (5.4), 113 (83), 95 (13), 81 (14), 71 (100), 57 (33), 43 (60), 29 (23).

Cis-penten-1-yl Cis-penten-1-yl used as starting material for the above preparation, was obtained as described for cis-hepten-1-yl bromide.

EXAMPLE 5

Ethyl 4-cis-hexenoate i. lithium metal (0.44 g.; 63 matomg.) containing 1.5% of sodium metal
ii. propen-1-yl bromide (3.87 g.; 32 mMole) containing 85% of the cis isomer
iii. trimethylphosphite iodocuprate (7.03 g.; 16 mMole) and
iv. ethyl acrylate (1.6 g.; 16 mMole)
were treated as shown in Example 3 for the preparation of ethyl 4-cis-decenoate. Distillation of the reaction mixture gave ethyl 4-cis-hexenoate (300 mg.; 16% yield). B.p. 54°–55°/11 Torr, with 100% isomeric purity and diethyl α-(cis-buten-2-yl)-glutarate (860 mg.; 21% yield), B.p. 83°–85°/0.05 Torr with 100% isomeric purity.

Ethyl 4-cis-hexenoate:
IR: 3010, 1730, 700 $cm^{-1}$
NMR: 1.22 (3H, t, J = 7 cps), 1.61 (3H, d, J = 5 cps), 2.25 (4H, m), 4.04 (2H, q, J = 7 cps), 5.33 (2H, m) δ ppm
MS: $M^+$ = 142 (46); m/e = 113 (6.8), 97 (43), 88 (42), 71 (67), 69 (98), 68 (100), 60 (48), 55 (84), 41 (86), 29 (76).

α-(cis-buten-2-yl)-glutarate:
IR: 3010, 1730 $cm^{-1}$
NMR: 1.22 (6H, t, J = 7 cps), 1.6 (3H, d, J = 5 cps), 1.7-2.4 (5H), 4.04 (4H, q, J = 7 cps), 5.2-5.5 (2H) δ ppm
SM: $M^+$ = 242 (< 1); m/e = 197 (45), 168 (68), 157 (16), 123 (42), 94 (100), 81 (50), 67 (15), 55 (42), 41 (18), 29 (49)

Propenyl bromide, used as starting material for the above preparation, was obtained as described in Example 1 for the preparation of cis-hepten-1-yl bromide.

EXAMPLE 6

4-cis-Octenal i. lithium metal (0.88 g.; 64 matomg.) containing 1.5% of sodium metal
ii. penten-1-yl bromide (9.5 g.; 64 mMole) containing 98% of the cis isomer
iii. trimethylphosphite iodocuprate (14.6 g.; 32 mMole) and
iv. freshly distilled acrolein (1.8 g.; 32 mMole)
were treated as described in Example 3. Distillation of the reaction mixture gave a colourless oil (1.7 g.) which contained 4-cis-octenal. A pure sample was obtained by preparative VPC.

IR: 3005, 2815, 2715, 1728 and 1685 $cm^{-1}$
NMR: 0.92 (3H, t, J = 6.5 cps), 1.8-2.5 (6H), 5.3 (2H, m), 9.67 (1H, t, J = 2 cps) δ ppm
MS: $M^+$ = 126 (0); m/e = 108 (3), 98 (9), 84 (56), 83 (38), 82 (42), 67 (69), 55 (82), 41 (100).

The following products were prepared by the same procedure as described in Example 1:

Ethyl 4-cis-heptenoate B.p. 68°/11 Torr
IR: 3010, 1735, 720 $cm^{-1}$
NMR: 1.03 (3H, t, J = 6 cps), 1.22 (3H, t, J = 7 cps), 1.8-2.4 (6H), 4.03 (2H, q, J = 7 cps), 5.3 (2H, m) δ ppm Ethyl 4-cis-nonenoate B.p. 100°/11 Torr
IR: 3010, 1735, 720 $cm^{-1}$
NMR: 0.89 (3H, t, J = 6 cps), 1.22 (3H, t, J = 7 cps), 1.8-2.4 (6H), 4.04 (2H, q, J = 7 cps), 5.3 (2H, m) δ ppm Ethyl 4-cis-undecenoate B.p. 129°/11 Torr
IR: 3010, 1735, 720 $cm^{-1}$
NMR: 0.89 (3H, t, J = 6 cps), 1.22 (3H, t, J = 7 cps), 1.8-2.4 (6H), 4.04 (2H, q, J = 7 cps), 5.3 (2H, m) δ ppm Methyl 4-cis-hexenoate B.p. 40°/11 Torr
IR: 3010, 1740, 720 $cm^{-1}$
NMR: 1.61 (3H, t, J = 5 cps), 2.25 (4H, m), 3.57 (3H, s), 5.3 (2H, m) δ ppm Methyl 4-cis-heptenoate B.p. 55°/11 Torr
IR: 3010, 1740, 720 $cm^{-1}$
NMR: 1.03 (3H, t, J = 6 cps), 1.7-2.3 (6H), 3.57 (3H, s), 5.3 (2H, m) δ ppm Methyl 4-cis-octenoate B.p. 72°/11 Torr
IR: 3010, 1740, 720 $cm^{-1}$
NMR: 0.9 (3H, t, J = 6 cps), 1.7-2.3 (6H), 3.52 (3H, s), 5.3 (2H, m δ ppm
MS: $M^+$= 156 (3); m/e = 141 (0), 124 (41), 113 (3), 96 (35), 82 (65), 74 (100), 67 (51), 59 (35), 55 (82), 41 (62)

Methyl 4-cis-nonenoate B.p. 85°/11 Torr
IR: 3010, 1740, 720 $cm^{-1}$
NMR: 0.89 (3H, t, J = 6 cps), 1.7-2.3 (6H), 3.58 (3H, s), 5.3 (2H, m) δ ppm Methyl 4-cis-decenoate B.p. 100°/11 Torr
IR: 3010, 1740, 725 $cm^{-1}$
NMR: 0.9 (3H), 1.8-2.4 (6H), 3.57 (3H, s), 5.3 (2H, m) δ ppm MS: M⁺ = 184 (4); m/e = 152 (27), 135 (7.7), 1,23 (10), 110 (54) 96 (29), 81 (35), 74 (100), 69 (52), 59 (33), 55 (67), 41 (68).

Methyl 4-cis-undecenoate B.p. 115°/11 Torr
IR: 3010, 1740, 725 cm⁻¹
NMR: 0.89 (3H), 1.8-2.4 (6H), 3.57 (3H, s), 5.3 (2H, m) δ ppm Methyl 4-cis-dodecenoate B.p. 130°/11 Torr
IR: 3010, 1740, 725 cm⁻¹
NMR: 0.89 (3H), 1.8-2.4 (6H), 3.57 (3H, s), 5.3 (2H, m) δ ppm Ethyl 2-trans-4-cis-hexadienoate B.p. 69°/11 Torr
IR: 3030, 1715, 1710, 1635, 1605, 990 cm⁻¹
NMR: 1.27 (3H, t, J = 7 cps), 1.89 (3H, d, J = 6 cps), 4.18 (2H, q, J = 7 cps), 5.84 (1H, d, J = 15 cps), 5.5-6.4 (2H, m), 7.62 (1H, d/d, J = 15 cps, J' = 11 cps) δ ppm
MS: M⁺ = 140 (50); m/e = 125 (34), 112 (12), 97 (81), 95 (100), 83 (5), 67 (99), 55 (10), 41 (60), 29 (28).

Ethyl 2-trans-4-cis-heptadienoate B.p. 85°–86°/11 Torr
IR: 3010, 1720, 1710, 1635, 1600, 990 cm⁻¹
NMR: 1.05 (3H, t, J = 7 cps), 1.26 (3H, t, J = 6 cps), 2.0-2.6 (2H, m), 4.1 (2H, q, J = 7 cps), 5.75 (1H, d, J = 15 cps), 5.5-6.3 (2H, m), 7.48 (1H, d/d, J = 15 cps, J' = 10.5 cps) δ ppm
MS: M⁺ = 154 (46); m/e = 125 (59), 109 (58), 97 (94), 81 (100), 67 (11), 53 (21), 41 (29), 29 (42).

Ethyl 2-trans-4-cis-octadienoate B.p. 100°/11 Torr
IR: 3020, 1720, 1705, 1635, 1605, 990, 700 cm⁻¹
NMR: 0.95 (3H, t, J = 6.5 cps), 1.27 (3H, t, J = 7 cps), 2.0-2.6 (2H, m), 4.13 (2H, q, J = 7 cps), 5.75 (1H, d, J = 15 cps), 5.5-6.4 (2H, m), 7.48 (1H, d/d, J = 15 cps, J' = 11 cps) δ ppm
MS: M⁺ = 168 (58); m/e = 153 (< 1), 139 (5.4), 125 (69), 111 (13), 97 (95), 95 (96), 81 (87), 67 (58), 55 (48), 39 (42) 29 (100).

Ethyl 2-trans-4-cis-nonadienoate B.p. 56°/0.05 Torr
IR: 3015, 1720, 1705, 1635, 1600, 990, 700 cm⁻¹
NMR: 0.93 (3H), 1.27 (3H, t, J = 7 cps), 2.0-2.6 (2H, m), 4.14 (2H, q, J = 7 cps), 5.77 (1H, d, J = 15 cps), 5.5-6.3 (2H, m), 7.5 (1H, d/d, J = 15 cps, J' = 11 cps) δ ppm Ethyl 2-trans-4-cis-undecadienoate B.p. 89°/0.05 Torr
IR: 3020, 1715, 1710, 1635, 1600, 990, 700 cm⁻¹
NMR: 0.9 (3H), 1.27 (3H, t, J = 7 cps), 2.0-2.5 (2H, m), 4.15 (2H, q, J = 7 cps), 5.8 (1H, d, J = 15 cps), 5.5-6.3 (2H, m), 7.55 (1H, d/d, J = 15 cps, J' = 11 cps) δ ppm Methyl 2-trans-4-cis-hexadienoate B.p. 57°/11 Torr
IR: 3010, 1720, 1710, 1640, 1605, 990, 705 cm⁻¹
NMR: 1.89 (3H, d, J = 6 cps), 3.65 (3H, s), 5.82 (1H, d, J = 15 cps), 5.5-6.4 (2H, m), 7.6 (1H, d/d, J = 15 cps, J' = 11 cps) δ ppm Methyl 2-trans-4-cis-heptadienoate B.p. 73°/11 Torr
IR: 3010, 1720, 1710, 1640, 1605, 990, 705 cm⁻¹
NMR: 1.05 (3H, t, J = 6.5 cps), 2.0-2.6 (2H, m), 3.65 (3H, s), 5.76 (1H, d, J = 15 cps), 5.5-6.4 (2H, m), 7.5 (1H, d/d, J = 15 cps, J' = 11 cps) δ ppm Methyl 2 trans-4-cis-octadienoate B.p. 88°/11 Torr
IR: 3010, 1720, 1710, 1640, 1605, 990, 705 cm⁻¹
NMR: 0.95 (3H, t, J = 6,5 cps), 2.0-2.6 (2H, m), 3.65 (3H, s), 5.76 (1H, d, J = 15 cps), 5.5-6.4 (2H, m), 7.5 (1H, d/d, J = 15 cps, J' = 11 cps) δ ppm Methyl 2-trans-4-cis-nonadienoate B.p. 46°/0.05 Torr
IR: 3010, 1720, 1710, 1640, 1605, 990, 705 cm⁻¹
NMR: 0.91 (3H), 2.0-2.6 (2H, m), 3.65 (3H, s), 5.76 (1H, d, J = 15 cps), 5.5-6.4 (2H, m), 7.5 (1H, d/d, J = 15 cps, J' = 11 cps) δ ppm Methyl 2-trans-4-cis-decadienoate B.p. 62°/0.05 Torr
IR: 3010, 1720, 1710, 1640, 1605, 990, 705 cm⁻¹
NMR: 0.9 (3H), 2.0-2.5 (2H, m), 3.67 (3H, s), 5.77 (1H, d, J = 15 cps), 5.5-6.3 (2H, m), 7.48 (1H, d/d, J = 15 cps, J' = 10 cps) δ ppm Methyl 2-trans-4-cis-undecadienoate B.p. 78°/0.05 Torr
IR: 3010, 1720, 1710, 1640, 1605, 990, 705 cm⁻¹
NMR: 0.9 (3H), 2.0-2.5 (2H, m), 3.67 (3H, s), 5.77 (1H, d, J = 15 cps), 5.5-6.3 (2H, m), 7.48 (1H, d/d, J = 15 cps, J' = 10 cps) δ ppm Methyl 2-trans-4-cis-dodecadienoate B.p. 95°/0.05 Torr
IR: 3010, 1720, 1710, 1640, 1605, 990, 700 cm⁻¹
NMR: 0.89 (3H7, 2.0-2.5 (2H, m), 3.67 (3H, s), 5.8 (1H, d, J = 15 cps), 5.5-6.3 (2H, m), 7.49 (1H, d/d, J = 15 cps, J' = 10 cps) δ ppm

EXAMPLE 7

3-Methyl-3-(cis-propen-1-yl)-1-cyclohexanone

Cis propen-1-yl bromide (5.32 g.; 44 mMole), containing 90% of the cis isomer, in anhydrous ether (30 ml.) was added at −10° in an argon atmosphere under vigourous stirring to a suspension of lithium metal (0.615 g,; 88 matomg.) containing 1.5% of sodium metal in anhydrous ether (30 ml.). The resulting solution was then added dropwise at −10° to a suspension of trimethylphosphite iodocuprate (10.0 g.; 23 mMole in anhydrous ether (20 ml.)

After complete dissolution of the cuprous complex, a solution of 3-methyl-2-cyclohexene-1-one (0.82 g.; 7.5 mMole) in anhydrous ether (5 ml.) was added dropwise to the reaction mixture under vigourous stirring. Once the reaction was over, stirring was continued for one more hour. Meanwhile the temperature raised to 0°. The reaction mixture was then poured onto a saturated aqueous ammonium chloride solution (100 ml.) and filtered on a diatomecious earth column. The organic layer was then extracted twice with ether and the combined organic extracts were successively washed with an aqueous ammonium chloride solution and a saturated aqueous sodium chloride solution then dried over magnesium sulfate and finally concentrated. The semi-cristalline residue was treated with hexane (100 ml.) and kept overnight at 0°. It was then collected by filtration on diatomaceous earth and the filtrate was concentrated and finally poured onto a silicagel column (50 g.) Elution with a 95 : 5 hexane-ether mixture gave, after evaporation of the volatile components, 3-methyl-3-(cis-propen-1-yl)-1-cyclohexanone (0.83 g.; 73% yield), B.p. 92°/11 Torr. The product contained 94% of the cis isomer. IR: 3010, 1705, 710 cm⁻¹
NMR: 1.17 (3H, s), 1.7 (3H, d, J, = 5 cps), 5.23 (2H, m) δ ppm
ms: M⁺ = 152 (127); m/e = 137 (64), 123 (34), 109 (79), 95 (95), 81 (50), 67 (97), 55 (100), 42 (89), 27 (36).

The following products were synthetized by the above described procedure:

3-methyl-3-(buten-1-yl)-1-cyclohexanone B.p. 94°/11 Torr
IR: 3010, 1710, 720 cm⁻¹

NMR: 0.90 (3H, t, J = 6 cps), 1.17 (3H, s), 5.2 (2H, m) δ ppm 3-methyl-3-(penten-1-cyclohexanone B.p. 60°/0.005 Torr IR: 3010, 1710, 720 cm⁻¹

NMR: 0.90 (3H, t, J = 6 cps), 1.17 (3H, s), 5.2 (2H, m) δ ppm 3-methyl-3-(hexen-1-yl)-1-cyclohexanone B.p. 130°/11 Torr IR: 3010, 1710, 725 cm⁻¹

NMR: 0.88 (3H, t, J = 6 cps), 1.17 (3H, s), 5.2 (2H, m) δ ppm

EXAMPLE 8

Perfume composition of the Chypre type

A Chypre type composition was prepared by admixing the following ingredients (parts by weight):

| | |
|---|---|
| Synthetic jasmine | 150 |
| Synthetic rose | 200 |
| Synthetic gardenia | 40 |
| Synthetic amber | 20 |
| Oak moss absolute | 20 |
| Musk ambrette | 30 |
| Musk ketone | 50 |
| Coumarine | 50 |
| Undecanal 10% sol.* | 80 |
| Methylnonenylacetic aldehyde 10% sol.* | 30 |
| Muscone 10% sol.* | 50 |
| Neroli Bigarade | 20 |
| Bergamot | 170 |
| Methylionone | 80 |
| Diethylphthalate | 10 |
| Total | 1000 |

*in diethyl phthalate

By adding 1.0 g. of ethyl 4-cis-decenoate to 99.0 g. of the above composition, the obtained composition had a new very agreable fruity character, particularly in the Chypre notes.

By substituting methyl or ethyl 4-cis-hexenoate, or methyl or ethyl 4-cis-heptenoate, or methyl 4-cis-decenoate for ethyl 4-cis-decenoate in the same proportions, the obtained compositions possessed a similar olfactive character.

By substituting methyl or ethyl 2-trans-4-cis-undecadienoate, or methyl or ethyl 2-trans-4-cis-dodecadienoate for ethyl 4-cis-decenoate in the same proportions, the obtained compositions presented an agreable ambrette fruity character, particularly in the Chypre notes. Moreover, esters of 2-trans-4-cis-dodecadienoic acid possess and confer a fatty note.

EXAMPLE 9

Preparation of a "Tutti-Frutti" type flavouring composition

A basic "Tutti-Frutti" type flavouring composition was prepared by admixing the following ingredients (parts by weight):

| | |
|---|---|
| Vanillin | 25 |
| Allyl caproate | 10 |
| Amyl butyrate | 35 |
| Ethyl butyrate | 75 |
| Ethyl acetate | 150 |
| Amyl acetate | 150 |
| Citral | 15 |
| Sweet orange oil | 50 |
| Lemon oil | 250 |
| Orange terpenes | 240 |
| Total | 1000 |

The above base composition was then used for manufacturing the following flavouring compositions

| | A | B | C |
|---|---|---|---|
| Tutti-Frutti base | 100 | 100 | 100 |
| Ethyl 2-trans-4-cis-heptadienoate | — | 5 | — |
| Ethyl 4-cis-decenoate | — | — | 5 |
| Ethyl alcohol 95% | 900 | 895 | 895 |
| | 1000 | 1000 | 1000 |

The above obtained compositions were then added to an acid sugar syrup in the proportions of 100 g. of flavour per 100 liters of syrup. The flavoured foodstuffs was then subjected to evaluation by a panel of flavour experts who defined the organoleptic character as follows: the foodstuffs flavoured with B and C had a heavier and fattier note than the one flavoured with A, and possessed a fruity, slightly floral character with a note reminiscent of pear, peach and strawberry fruits. In the base composition ethyl 2-trans-4-cis-heptadienoate was then replaced by the following compounds in the given proportions (parts by weight):

| | |
|---|---|
| 1. ethyl 2-trans-4-cis-hexadienoate | 100 |
| 2. ethyl 2-trans-4-cis-heptadienoate | 100 |
| 3. ethyl 2-trans-4-cis-dodecadienoate | 100 |
| 4. 3-methyl-3-(cis-propen-1-yl)-1-cyclohexanone | 300 |

The new flavoured foodstuffs were then tested as mentioned before and the following organoleptic characters were observed:

1. sweet, fruity, pear character
2. fatty, sweet, green, fruity
3. fatty, slightly fruity, pear character
4. caraway

EXAMPLE 10

Preparation of methyl 2-pentenyl-3-oxo-cyclopentylacetate i. lithium metal (0.028 g; 4 mMole) containing 1.5 % of sodium metal
ii. cis-buten-1-yl bromide (0.270 g; 2mMole)
iii. copper(I)-iodide (1 mMole), and a
iv. mixture of 2-methylene- and 4-methylene-3-oxo-cyclopentyl-acetic acid methyl ester were treated according to the procedure as given in Example 1. The resulting reaction mixture afforded by bulb distillation 0.114 g (53 %) of the desired ester, the physical data of which were in agreement with those published in J.Org.Chem., 36, 2021 (1971) for a pure sample.

The mixture of 2-methylene- and 4-methylene-3-oxo-cyclopentaylacetic acid methyl ester, used as starting material in the above preparation, can be prepared as follows:

Methyl 3-oxo-cyclopentylacetate (1.56 g; 10 mMole) [prepared according to the procedure described in Helv. Chim. Acta, 45, 692 (1962)], piperidine hydrochloride (1.24 g; 10 mMole) and an aqueous solution of formaldehyde (1.1 ml; 40 % solution; 10 mMole) were stirred for 30 minutes at 75°–80° and 30 more minutes at room temperature. The reaction mixture was then distilled by bulb distillation at 0.07 Torr to afford 0.355 g of starting material (22 %; 90°–120°). The cristallized residue was dissolved in a 10 % aqueous potassium hydroxide solution and extracted then with diethyl ether, and the combined extracts were washed with water, dried over magnesium sulfate and evaporated to dryness.

On distillation the obtained residue afforded 0.180 g of a ca. 1:1 mixture of 2-methylene- and 4-methylene-3-oxo-cyclopentylacetic acid methyl ester; b.p. 130°–150°10.07 Torr; yield 10 %.

NMR: 2.0-2.7 (7 H); 3.6 (3 H, s); 3.63 (3 H, s); 5.2 (1 H, m); 5.84 (1H, m); δ ppm IR (CCl$_4$): 2955, 1735, 1640, 1433, 1407 cm$^{-1}$ MS: 168 (42); 149 (6); 140 (67); 137 (40); 125 (16); 108 (69); 95 (100); 81 (50); 67 (59); 53 (50); 41 (53); 27 (39).

EXAMPLE 11

Preparation of ethyl 2-cis-4-cis-undecadienoate

The product has been prepared in accordance with the procedure described in example 1. The analytical data were as follows:

IR (neat liquid): 2930, 2860, 1719, 1632, 1590, 1665, 1441, 1419, 1368, 1302, 1267, 1229, 1188, 1163, 1137, 1093, 1031, 997, 960, 946, 928, 869, 827, 788, 723, 690, 626 cm$^{-1}$ MS: M$^+$= 210; m/e: 181 (1); 165 (19); 153 (6); 136 (11); 125 (100); 107 (13); 97 (71); 81 (60); 67 (75); 55 (43); 41 (54); 29 (76).

UV (EtOH): λ max = 267 mμ (ε= 20,750).

The following products were prepared by the same procedure as described in example 1:

4,4-dimethyl-hepten-5-one-2, cis: B.p. 110°–140°/740 Torr;

IR (neat liquid): 3010, 1710, 710 cm$^{-1}$

NMR: 1.19 (6H,s); 1.7 (3H,d, J=5.5 cps); 2.01 (3H,s); 2.45 (2H,s); 5.25 (2H,m) δ ppm.

5-cis-nonen-2-one: B.p. 60°/11 Torr;

IR (neat liquid): 3010, 1712, 710 cm$^{-1}$

NMR: 0.9 (3H, t, J=6 cps); 2.04 (3H,s); 5.3 (2H,m) δ ppm.

We claim:

1. A process for modifying, improving or enhancing the olfactory properties of perfume compositions which comprises adding thereto an effective fragrance amount of at least one compound of formula

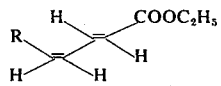

wherein R represents an alkyl radical containing 1 or from 4-7 carbon atoms.

2. A process according to claim 1 in which ethyl 2-trans-4-cis-undecadienoate is added to the perfume compositions.

3. A process according to claim 1 in which ethyl 2-trans-4-cis-dodecadienoate is added to the perfume compositions.

4. A process according to claim 1 in which ethyl 2-trans-4-cis-decadienoate is added to the perfume or perfumed products.

* * * * *

UNITED STATES PATENT AND TRADEMARK OFFICE
CERTIFICATE OF CORRECTION

PATENT NO. : 3,953,377

DATED : April 27, 1976

INVENTOR(S) : Ferdinand Naf

It is certified that error appears in the above-identified patent and that said Letters Patent are hereby corrected as shown below:

Column 1, lines 17, 38 and 67 "$R^3_n \quad R^4_n$" should be -- $R^3_n \quad R^4_n$ --

Column 1, line 29 "zero of" should be --zero or--

Column 7, line 7 "$CH=C-CO-CH_3$" should be --$CH\equiv C-CO-CH_3$--

Column 7, lines 57-60 "$X - \underset{\underset{R^3_n}{|}}{\overset{\overset{R^5}{|}}{C^\beta}} = \underset{\underset{R^4_n}{|}}{\overset{}{\overset{\alpha}{C}H}} - \overset{\overset{O}{\|}}{C} - (O)_m R^7$"

should be --

$$X - \underset{\underset{R^3_n}{|}}{\overset{\overset{R^5}{|}}{C^\beta}} {=\!=\!=} \underset{\underset{R^4_n}{|}}{\overset{\alpha}{C}H} - \overset{\overset{O}{\|}}{C} - (O)_m R^7$$

--

UNITED STATES PATENT AND TRADEMARK OFFICE
CERTIFICATE OF CORRECTION

PATENT NO. : 3,953,377

DATED : April 27, 1976

INVENTOR(S) : Ferdinand Naf

It is certified that error appears in the above-identified patent and that said Letters Patent are hereby corrected as shown below:

Column 8, line 60 "Ii" should be --II--

Column 13, line 35 "Cis-penten-1-yl Cis-penten-1-yl" should be --Cis-penten-1-yl bromide--

Column 14, line 57 "(2H,m δppm" should be --(2H,m)δ ppm--

Column 16, line 61 "ms" should be --MS--

Column 17, line 3 "(penten-1-cyclohexanone" should be --(penten-1-yl)-1-cyclohexanone--

Column 18, line 55 "cyclopentaylacetic" should be --cyclopentylacetic--

Column 19, line 7 "150°10.07 Torr" should be --150°/0.07 Torr--

Signed and Sealed this

Fourteenth Day of September 1976

[SEAL]

Attest:

RUTH C. MASON
*Attesting Officer*

C. MARSHALL DANN
*Commissioner of Patents and Trademarks*